(12) United States Patent
Conteduca et al.

(10) Patent No.: US 6,245,073 B1
(45) Date of Patent: *Jun. 12, 2001

(54) RETAINER FOR TENDONS USED IN THE RECONSTRUCTION OF THE ANTERIOR CRUCIATE LIGAMENT OF THE KNEE

(75) Inventors: Fabio Conteduca; Andrea Ferretti, both of Rome (IT)

(73) Assignee: Citieffe S.r.l., Calderara di Reno (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/057,492

(22) Filed: Apr. 9, 1998

(51) Int. Cl.[7] .................................................. A61B 17/156
(52) U.S. Cl. .............................................. 606/72; 606/232
(58) Field of Search ................................. 606/72, 70, 71, 606/79, 73, 96, 88, 86, 232; 623/13

(56) References Cited

U.S. PATENT DOCUMENTS

| | | | |
|---|---|---|---|
| 4,870,957 | * 10/1989 | Goble et al. | 606/72 |
| 4,932,868 | * 6/1990 | Linkow et al. | 433/174 |
| 5,053,034 | * 10/1991 | Olerud | 606/61 |
| 5,152,790 | * 10/1992 | Rosenberg et al. | 623/13 |
| 5,356,413 | * 10/1994 | Martins et al. | 606/75 |
| 5,376,119 | * 12/1994 | Zimmermann et al. | 606/72 |
| 5,391,170 | * 2/1995 | McGuire et al. | 606/86 |
| 5,423,860 | * 6/1995 | Lizardi et al. | 606/75 |
| 5,514,159 | * 5/1996 | Matula et al. | 606/232 |
| 5,562,668 | * 10/1996 | Johnson | 606/72 |
| 5,571,184 | 11/1996 | DeSatnick . | |

FOREIGN PATENT DOCUMENTS

| | | | |
|---|---|---|---|
| 296 20 735 U | 1/1997 | (DE) . | |
| 29620735 | * 1/1997 | (DE) | 606/72 |
| 2288739 | * 11/1995 | (GB) | 606/72 |
| 9216167 | 10/1992 | (WO) . | |
| 9216167 | * 1/1997 | (WO) | 606/72 |

* cited by examiner

*Primary Examiner*—Henry J. Recla
*Assistant Examiner*—Lien Ngo
(74) *Attorney, Agent, or Firm*—Guido Modiano; Albert Josif; Daniel O'Byrne

(57) ABSTRACT

The retainer for tendons used in the reconstruction of the anterior cruciate ligament of the knee comprises a cylindrical body having a flange at one end and an eyelet at the other end; the tendons are engaged through the eyelet and are guided through a hole formed through the femoral and tibial condyles; the body can be inserted until the flange abuts against the femoral inlet of the hole.

6 Claims, 6 Drawing Sheets

RETAINER FOR TENDONS USED IN THE RECONSTRUCTION OF THE ANTERIOR CRUCIATE LIGAMENT OF THE KNEE

BACKGROUND OF THE INVENTION

The present invention relates to a retainer for tendons used in the reconstruction of the anterior cruciate ligament of the knee.

The conventional method for reconstructing the anterior cruciate ligament of the knee entails drilling a hole that passes through the tibial and femoral condyles. A frame, provided with slots for the passage of two tendons recovered from the tendinous muscle and from the gracilis muscle, is driven through the tibial inlet of the hole. When the frame has exited from the femoral inlet of the hole, it is orientated diametrically to said hole and the tendons are pulled and anchored to the tibial cortex.

The retainer according to the prior art entails the substantial drawback that it does not allow to correctly tension the bundles of tendons. Tendon tensioning in fact occurs simultaneously with their fixation and can no longer be adjusted once fixation has been completed.

SUMMARY OF THE INVENTION

The technical aim of the present invention is to provide a new retainer which allows to eliminate the above drawbacks.

Within the scope of this aim, an object of the present invention is to provide a retainer which is capable of facilitating the operating technique for its installation.

This aim and this object are achieved by a retainer for tendons used in the reconstruction of the anterior cruciate ligament of the knee, characterized in that it comprises a cylindrical body having a flange at one end and an eyelet at the other end, the tendons being engaged through said eyelet and being guided through a hole formed through the femoral and tibial condyles, said body being insertable until said flange abuts against the femoral inlet of said hole.

BRIEF DESCRIPTION OF THE DRAWINGS

Further particularities of the retainer according to the invention will become apparent from the following description on the basis of the accompanying drawings, wherein.

DESCRIPTION OF THE PREFERRED EMBODIMENTS

Figure 1:
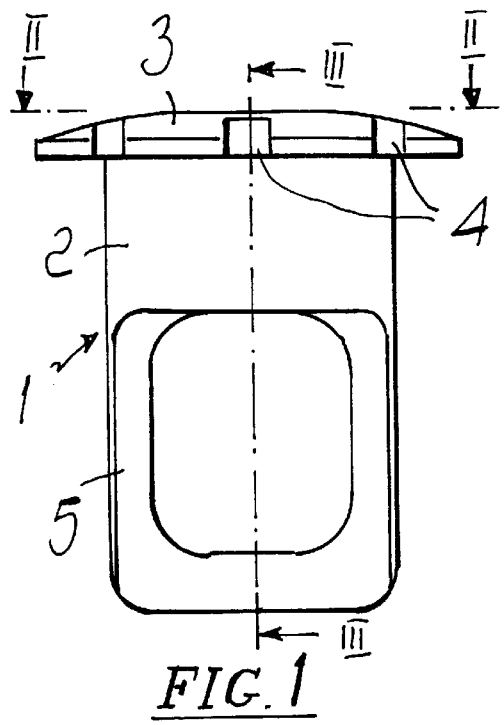
FIG. 1 is a side view of a retainer according to a first embodiment.
Figure 2:
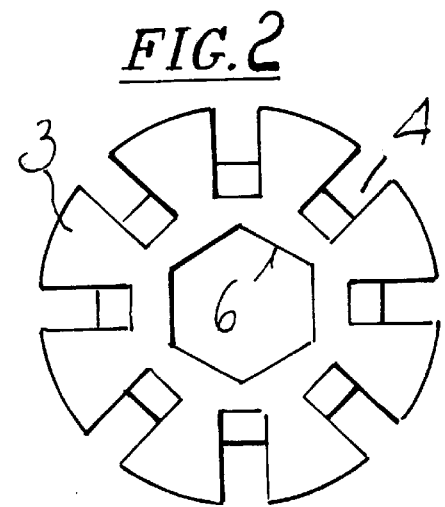
FIG. 2 is a sectional view, taken along the plane II—II of FIG. 1.
Figure 3:
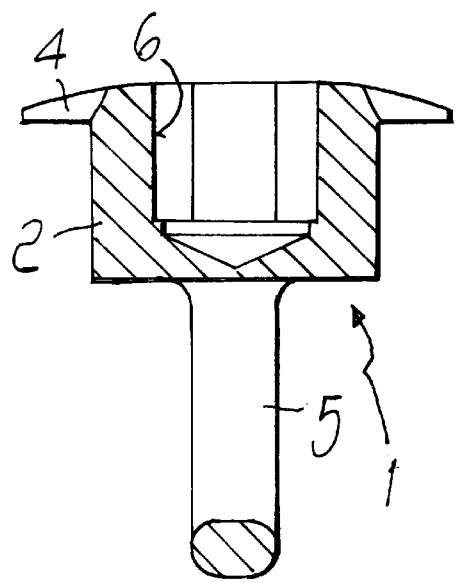
FIG. 3 is a sectional view, taken along the plane III—III of FIG. 1.

With reference to the above FIGS. 1–3, the retainer is generally designated by the reference numeral 1 and comprises a cylindrical body 2 having, at one end, a cambered flange 3. A plurality of notches 4 are formed in the flange 3, are diametrically mutually opposite to the axis of the body 1 and are angularly mutually equidistant.

A quadrangular eyelet 5 protrudes from the opposite side of the body 2 with respect to the flange 3. The eyelet 5 lies on a diametrical plane that passes through the axis of the body 1 and has a substantially ellipsoidal cross-section.

The described retainer is completed by a hexagonal recess 6 which is formed axially in the body 1 and is open at the center of the flange 7. The recess 6 is meant for the engagement of a tool, for example an Allen wrench, whereby the retainer can be turned once it has been installed in the seat meant to receive it.

The method for installing the described retainer is as follows.

The semitendinous tendon B and the gracilis tendon C are first released through an incision A formed with an arthroscope; however, said tendons remain inserted on the tibia with one end. Two sutures D, for example of the type known as Brunnel suture, are then applied to the free ends of the two tendons B and C to allow the coupling of the thread E for pulling the tendons through the articulation of the knee.

Figure 5:
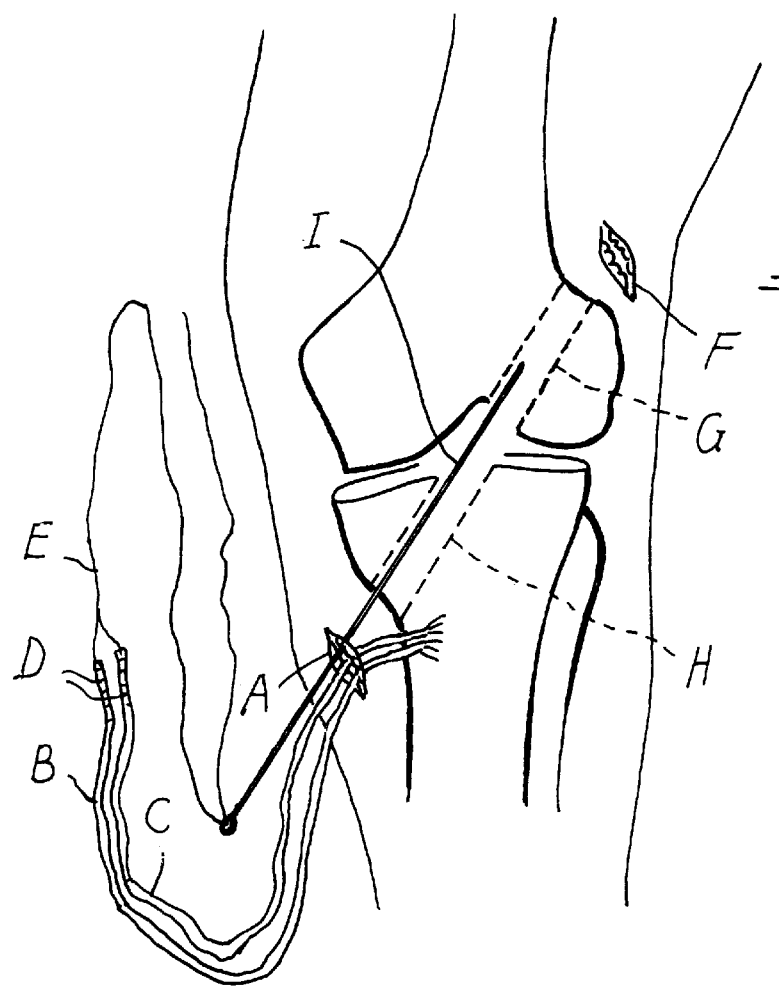
FIGS. 5 to 13 are views of various steps of the installation of the retainer.

The arthroscope is then reinserted through a second supracondylar incision F and is used to form, according to conventional methods, the outer percondylar hole G and the tibial hole H (FIG. 5).

Figure 6:
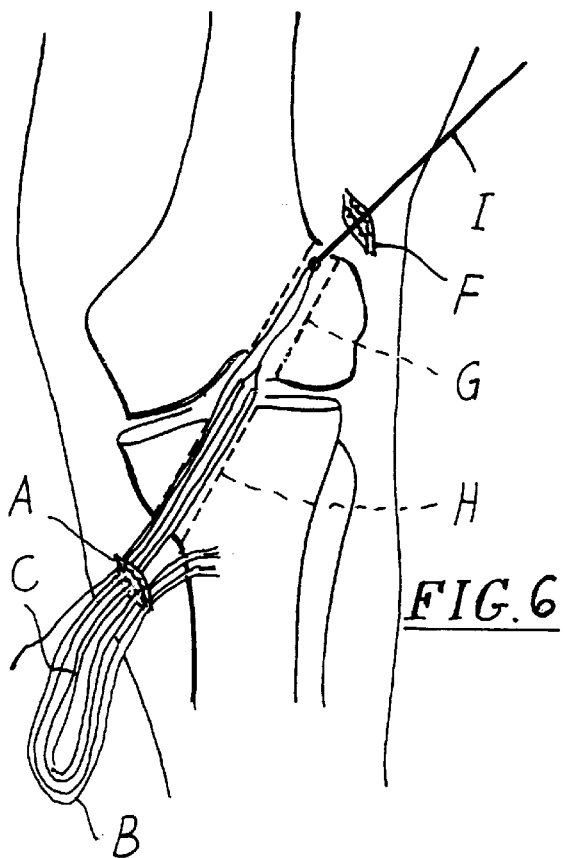
Figure 7:
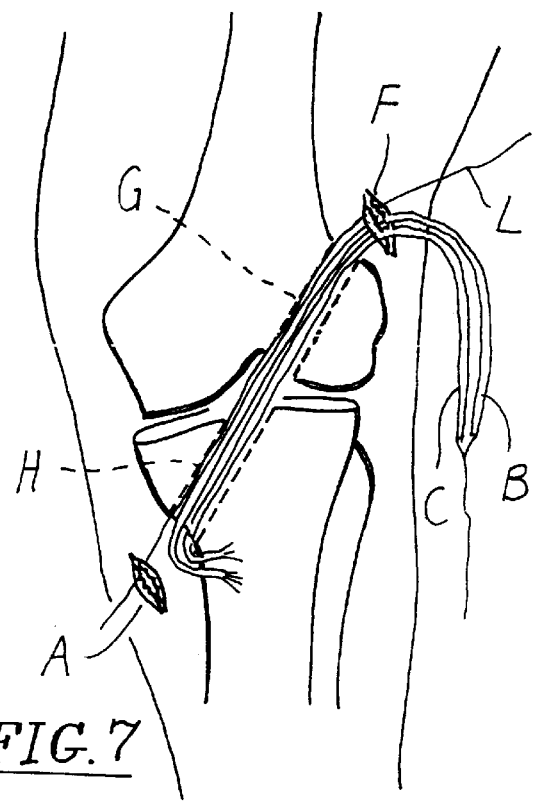

By using a suitable ligature carrier I, the tendons B and C are then passed through the tibial hole H and through the femoral hole G until they fully exit from the incision F (FIGS. 6, 7).

Figure 8:
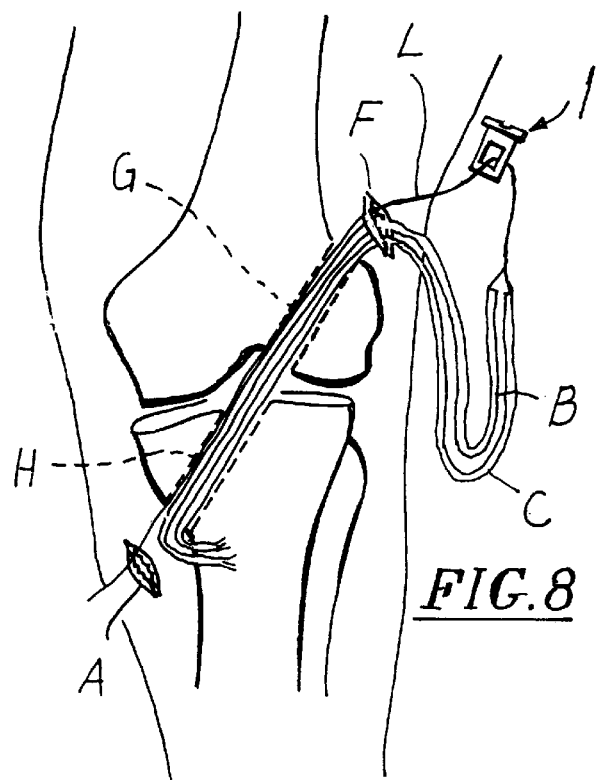

At this point, the tendons B and C are guided through the eyelet 5 of the retainer 1 (FIG. 8).

Figure 9:
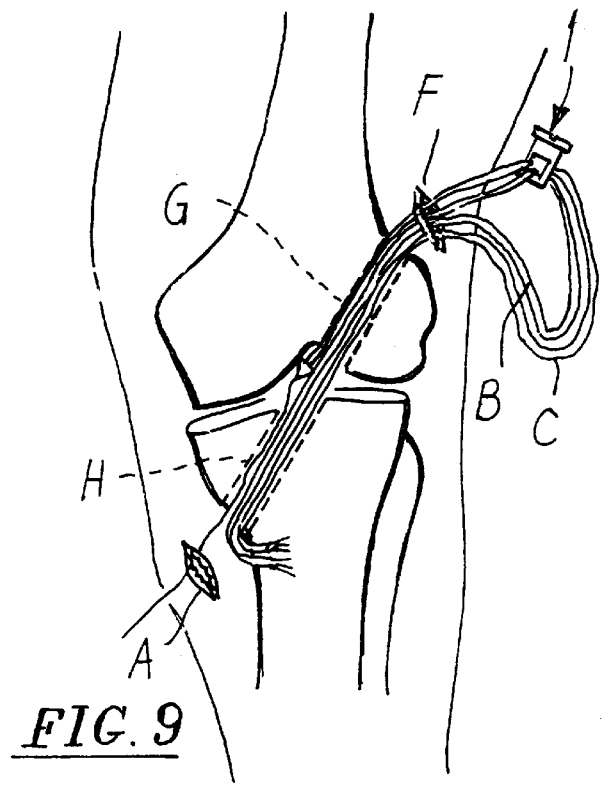

By using a second traction wire L, the tendons are reinserted in the femoral hole G and in the tibial hole H, until they again exit from the tibial hole H (FIGS. 8 and 9).

Figure 10:
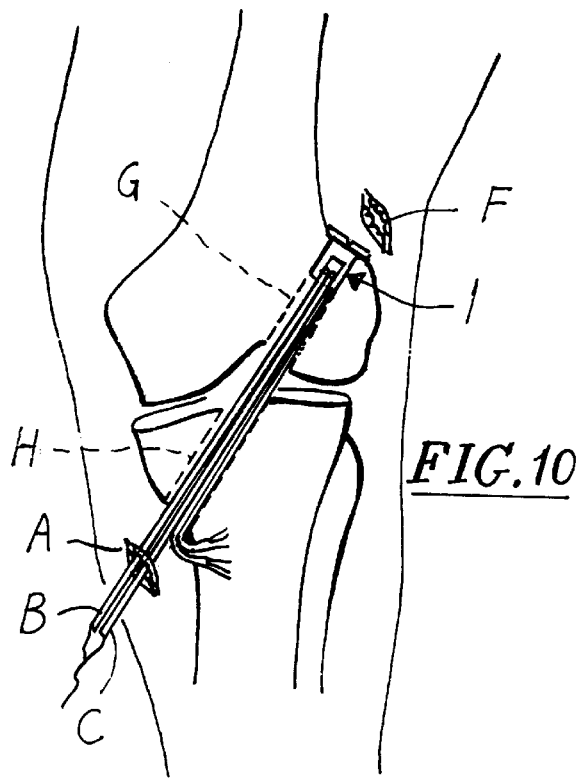

The traction applied by the tendons to the retainer 1 causes the partial engagement of the retainer 1 in the inlet of the femoral hole G. By using a suitable boneset, the retainer is fully inserted in the femoral hole G until the flange 3 abuts against the outer cortex of the femur (FIG. 10). An adequate traction of the free ends of the tendons allows them to slide on the eyelet 5.

Figure 11:
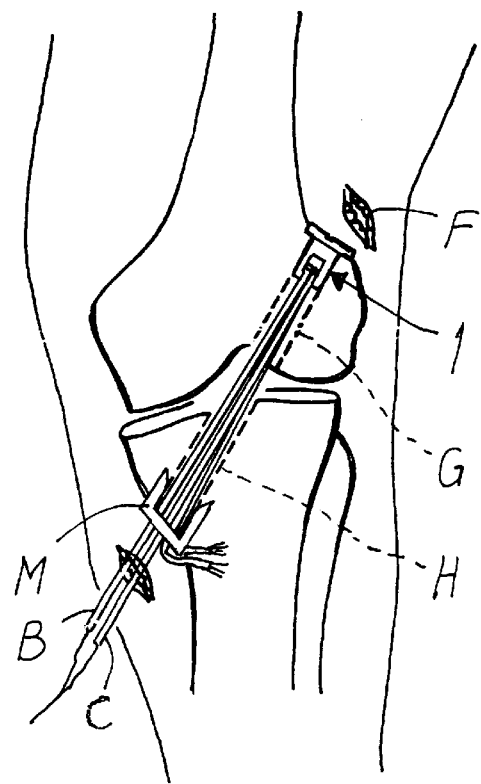

When the pretensioning of all four bundles of tendons has reached a preset value, one and two staples M (FIG. 11) are arranged so as to straddle the tendons at the exit of the tibial hole H. At this point, valid stabilization of the knee has already been achieved.

Figure 12:
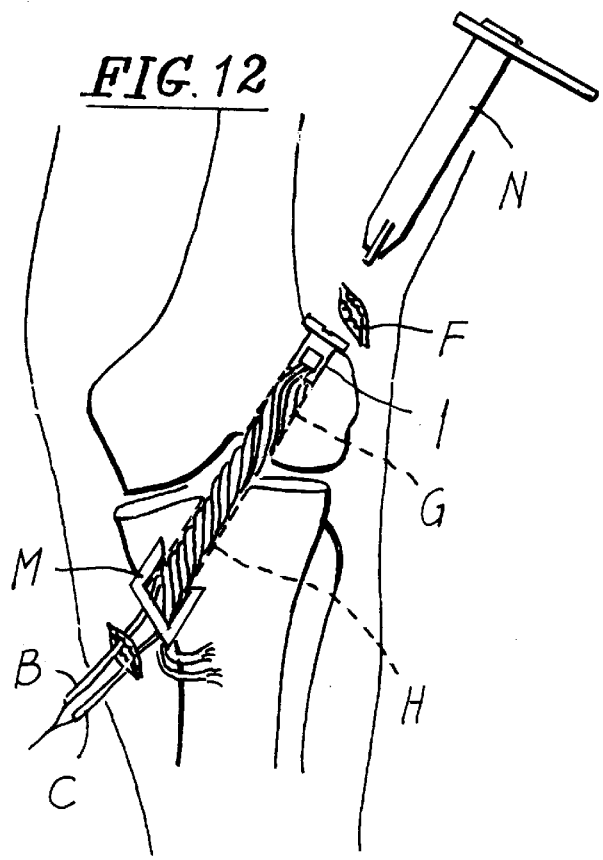

However, the retainer allows an additional and final tensioning by twining the tendon bundles inside the femoral hole G and the tibial hole H. For this purpose, an Allen wrench N is inserted in the recess 6 and turned through the necessary angle, for example approximately 360° (FIG. 12). The direction of rotation of the tendon bundles is clockwise for the right knee and counterclockwise for the left knee. The tensioning force of the tendons can be controlled with a torque wrench.

Figure 13:
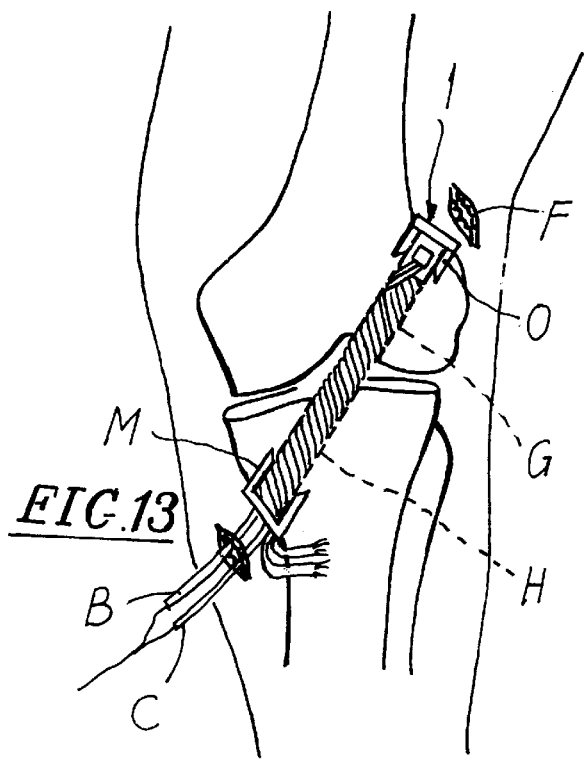

When the tendons have reached the intended tension, the retainer 1 is fixed against possible rotary and axial displacements by positioning a staple O so as form a bridge on the flange 3, so that the teeth of the staple O engage the notches 4 (FIG. 13).

It is evident that the described retainer perfectly achieves the intended aim and object. In particular, the retainer allows to simultaneously perform pretensioning and final tensioning of the tendons during the operation, at the chosen degrees of flexing and for the time deemed most suitable by the operator, allowing to take advantage of the visco-elastic properties of tendons.

Figure 4:
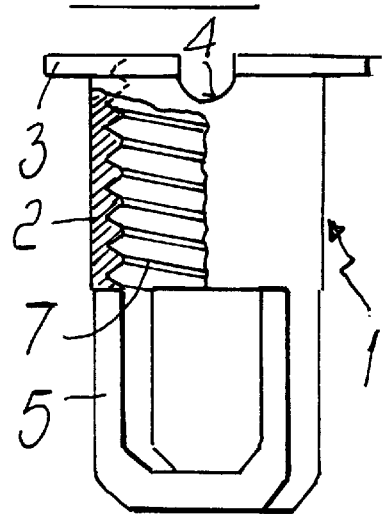
FIG. 4 is a partially sectional side view of a different embodiment of the retainer.

According to a different embodiment of the invention, illustrated in FIG. 4, instead of the hexagonal recess 3 a threaded hole 7 is provided which is suitable to receive a screw-on plug that, by preventing the growth of bone inside its internal hole, facilitates the optional engagement of a tool for the removal of the retainer, if and when required.

In a further embodiment, the eyelet 5 is open so as to form a sort of hook.

What is claimed is:

1. A method of using a retainer for tendons used in the reconstruction of the anterior cruciate ligament of the knee, the retainer comprising a cylindrical body having a flange at one end and an eyelet at the other end, said flange and said eyelet being rigidly connected with said cylindrical body such that when said cylindrical body is rotated about its axis said flange and said eyelet rotate together with said cylindrical body, the method of using the retainer comprising the steps of engaging the tendons through said eyelet and guiding the tendons through a hole formed through the femoral and tibial condyles, and inserting said cylindrical body until said flange abuts the femoral inlet of said hole wherein said body has a recess for the engagement of a tool in which said method makes said body turn in said hole such that said tendons engaged in said eyelet are mutually twined together.

2. A method of using a retainer according to claim 1, wherein said recess has a hexagonal cross-section.

3. A method of using a retainer according to claim 1, wherein said recess is a threaded hole which receives a closure plug by screwing.

4. A method of using a retainer according to claim 1, wherein said flange has radial notches which are engaged by means for fixing the retainer against rotary and axial movements.

5. A method of using a retainer a retainer according to claim 1, wherein said eyelet is open so as to form a sort of hook.

6. A method of using a retainer according to claim 1, wherein said tendons have a first end fixed in an area adjacent the tibia, and said tendons extend from said area adjacent the tibia through a tibial hole and through an outer percondylar hole and through said eylet and then back through said outer percondylar hole and said tibial hole, and said tendons have a second end fixed at said area adjacent the tibia.

* * * * *